United States Patent [19]

Price

[11] 4,102,922

[45] Jul. 25, 1978

[54] PURIFICATION OF CARBONYLATION PRODUCTS

[75] Inventor: Jerry L. Price, Texas City, Tex.

[73] Assignee: Monsanto Company, St. Louis, Mo.

[21] Appl. No.: 731,594

[22] Filed: Oct. 12, 1976

Related U.S. Application Data

[63] Continuation of Ser. No. 537,500, Dec. 30, 1974, abandoned.

[51] Int. Cl.$^2$ ..................... C07C 51/10; C07C 51/12; C07C 51/44; C07C 67/36
[52] U.S. Cl. ................................... 260/532; 260/410; 260/410.9 R; 260/413; 260/419; 260/514 M; 260/515 P; 260/515 R; 260/525; 260/533 AN; 260/537 R; 260/540; 260/541; 560/78; 560/79; 560/97; 560/105; 560/109; 560/114; 560/191; 560/204; 560/232; 560/233
[58] Field of Search ............. 260/514 M, 468 M, 532, 260/488 K, 496, 491, 493, 413, 419, 540, 541, 410.9 R, 410; 560/232, 114

[56] References Cited

U.S. PATENT DOCUMENTS

| 3,769,329 | 10/1973 | Paulik et al. ...................... 260/488 K |
| 3,772,380 | 11/1973 | Paulik et al. ...................... 260/488 K |
| 3,845,121 | 10/1974 | Eubanks et al. .................. 260/488 K |

*Primary Examiner*—Vivian Garner
*Attorney, Agent, or Firm*—James C. Bolding; Elizabeth F. Sporar; Paul L. Passley

[57] ABSTRACT

A method is provided for the removal of contaminating alkanes from the vaporized carbonylation products of a process wherein carboxylic acids are produced by the reaction in the liquid phase of an alcohol or an ester, halide or ether derivative of said alcohol with carbon monoxide in the presence of a catalyst system containing a rhodium or iridium component and an iodine or bromine component. The method involves distillation of the alkane-containing vaporized carbonylation products, phase separation of the overhead from said distillation, further distillation of a slipstream of the resulting heavy phase using carbon monoxide as stripping gas and removal of the alkanes as the bottoms stream from the latter distillation.

7 Claims, 1 Drawing Figure

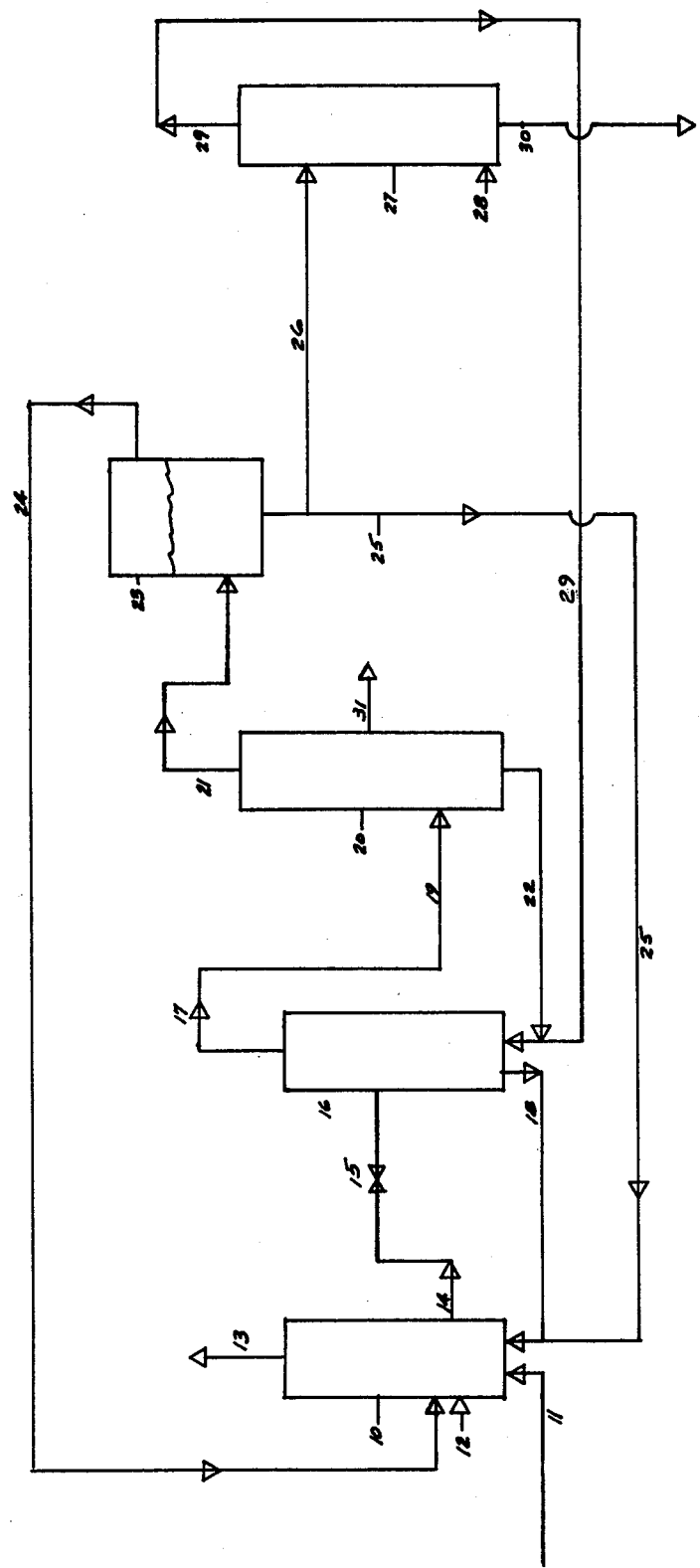

4,102,922

PURIFICATION OF CARBONYLATION PRODUCTS

BACKGROUND OF THE INVENTION

The present invention relates to a carbonylation process improvement. More particularly, this invention relates to an improved process scheme wherein alkanes are removed from carbonylation products.

Recently, processes for producing carboxylic acids and esters by carbonylating olefins, alcohols, esters, halides and ethers in the presence of homogeneous catalyst systems that contain rhodium or iridiium and halogen components such as iodine components and bromine components have been disclosed and placed into commercial operation. These recently developed processes represent a distinct improvement over the classic carbonylation processes wherein such feed materials have been previously carbonylated in the presence of such catalyst systems as phosphoric acid, phosphates, activated carbon, heavy metal salts and metal carbonyls such as cobalt carbonyl, iron carbonyl and nickel carbonyl. All of these previously known processes require the use of extremely high partial pressures of carbon monoxide. These previously known carbonylation systems also have distinct disadvantages in that they require higher catalyst concentrations, longer reaction times, higher temperatures to obtain substantial reaction and conversion rates that all result in larger and more costly processing equipment and higher manufacturing costs.

The discovery that rhodium or iridium and iodine- or bromine-containing catalyst systems will carbonylate such feed materials as olefins, alcohols and ester, halide or ester derivatives of the alcohols at relatively mild pressure and temperature conditions was a distinct contribution to the carbonylation art. In spite of the vast superiority of these newly developed catalyst systems, it was found that conventional processing schemes for separation of the carbonylation products from the liquid reaction mass posed problems of catalyst inactivation and precipitation. In U.S. Pat. No. 3,845,121, an improved process scheme is described wherein carbonylation products can be recovered from a carbonylation reaction zone without resulting in decomposition of the catalyst system when the liquid-phase active catalyst and unreacted feed components are recycled to the reaction zone. According to this process, the carbonylation rection is carried out in the reaction zone at a temperature from about 50° to 150° C and a pressure from about 50 to 1500 psia and at least a portion of the liquid reaction mass is passed to a separation zone without the addition of heat, said separation zone having a pressure of at least 20 psi less than the pressure in said reaction zone to vaporize at least a portion of the carbonylation products, the vaporized carbonylation products being withdrawn and the remaining liquid reaction mass being recycled to said reaction zone.

The vaporized product obtained in the process of U.S. Pat. No. 3,845,121 is passed to a conventional purification system of multiple distillation columns for ultimate recovery of the carboxylic acid in pure form. However, certain difficulties arise during such purification which are attributable to the presence in the system of alkanes typical among which are those having from 6 to 12 carbon atoms and which are straight-chain compounds such as hexane, heptane, octane, decane and the like. Alkanes can enter the carboxylic acid production facilities from several sources among which are the carbon monoxide and the methanol feed streams. The alkanes azeotrope or steam distill with water and are soluble in methyl iodide. They create problems in the reaction zone in that a second phase containing alkanes, methyl iodide and acetic acid is generated therein. In addition, the alkanes appear in the heavy phase from the overhead of the column used to remove the light ends from the reaction effluent. This heavy phase is normally recycled to the reactor. In addition, to the fact that the presence of alkanes therein has a tendency to overload the heavy phase pump due to dramatic density changes, these unwanted compounds tend to load down the light ends column itself thus limiting plant capacity. There is no way out of the system for these alkanes except by actual spills and thus a need for a method for their removal is created.

It is an object of the present invention, therefore, to provide a method for the removal of alkanes in a process wherein carboxylic acids are produced by the reaction of an alcohol or olefin with carbon monoxide in the presence of a rhodium- or iridium-containing catalyst system and recovered therefrom by distillation.

Other objects and advantages of the invention will become apparent from the following discussion of the invention.

SUMMARY OF THE INVENTION

The present invention relates to an improvement in the process wherein an alcohol or an ester, halide or ether derivative of said alcohol is reacted with carbon monoxide in the liquid phase in the presence of a catalytic system that contains a rhodium or iridium component and an iodine or bromine component, a portion of the liquid reaction mass is passed to a separation zone without the addition of heat, said separation zone having a pressure of at least 20 psi less than the pressure in said reaction zone, to vaporize at least a portion of the carbonylation products, the remaining liquid reaction mass is recycled to the reaction zone, and the vaporized carbonylation products are withdrawn and subjected to distillation for recovery of carbonylation products therefrom. The improvement comprises removing alkanes from the purification system by introducing said vaporized carbonylation products into a first distillation zone to remove an overhead product and a bottoms product, separating said overhead product into a light phase and a heavy phase, removing a slipstream of said heavy phase, introducing it into a second distillation zone and distilling so as to remove an overhead stream free of alkanes and a bottoms stream consisting substantially of alkanes, and recycling said alkane-free overhead stream to the separation zone. The bottoms product from the first distillation zone can be recycled to the separation zone, while the light phase and the major part of the heavy phase from the overhead product of the first distillation column can both be recycled to the reactor.

DESCRIPTION OF THE PREFERRED EMBODIMENTS

To further describe the present invention, reference is made to the accompanying drawing, which represents a schematic diagram of the process of the invention wherein methanol is carbonylated in the presence of a rhodium- or iridium-containing catalyst system. By way of example, the catalyst system can be formed by introducing rhodium iodide and hydrogen iodide into reactor 10 that has been partially filled with acetic acid and water as a reaction medium. Carbon monoxide can be sparged into the reactor through line 11. Methanol feed is introduced into the reactor through line 12. The reactor is maintained at a temperature of from about 160° to about 220° C and the pressure in the reactor is maintained from about 200 to 750 psig. Unreacted carbon monoxide, along with any gaseous impurities or by-products can be withdrawn from the reactor through line 13.

A portion of the liquid reaction mass is withdrawn from reactor 10 through line 14. Pressure let-down valve 15 is disposed in line 14 to let the pressure down at least 20 psi as it enters separation zone 16. As the reaction mass enters separation zone 16, a portion of the carbonylation products vaporize and can be withdrawn from the separation zone through line 17. The remaining liquid reaction mass containing the catalyst system in separation zone 16 can be recycled to reactor 10 via line 18. The vapors withdrawn from the separation zone through line 17 are introduced into distillation zone 20 via line 19 and distilled therein to remove an overhead product and a bottoms product. The bottoms product consisting mainly of acetic acid with some water and a small amount of hydrogen iodide is recycled to the separation zone via line 22. The overhead product which contains water, acetic acid, a major proportion of methyl iodide and alkalines is withdrawn through line 21, condensed and passed to separator 23 where it is allowed to settle to form two phases. The light phase consisting essentially of acetic acid and water is returned to the reactor 10 via line 24. The major part of the heavy phase consisting of methyl iodide, acetic acid, water and alkanes is returned to the reactor 10 via line 25. To effect removal of the alkanes, a slipstream 26 representing about 1% or less by weight of the total heavy phase is withdrawn through line 26 and introduced into distillation zone 27 at the upper end thereof while a stream of carbon monoxide is fed through line 28 to facilitate stripping of the methyl iodide from the alkane mixture. An overhead product substantially free of alkanes and consisting predominantly of methyl iodide with some acetic acid is withdrawn through line 29 and recycled to the separation zone 16. The bottoms product consisting essentially of alkanes, some acetic acid and traces of methyl iodide leaves the system through line 30 and is sent to waste disposal facilities. Crude acetic acid leaves the system through line 31 and is passed to downstream distillation for further purification.

The basic process for the production of carboxylic acids and esters to which the present invention applies is described in full detail and claimed in U.S. Pat. Nos. 3,769,329 and 3,772,380, both of which are incorporated herein by reference. The separation of the carbonylation products from the reaction mixture without catalyst deomposition as has been mentioned earlier is described and claimed in U.S. Pat. No. 3,845,121, which is likewise incorporated herein by reference. The process of the present invention constitutes an improvement whereby alkanes are removed from the product obtained when preparing carboxylic acids using the process resulting from combination of methods described in the above-mentioned patents.

In the process of the present invention briefly described above and illustrated in the drawing, the distillation zones can comprise any distillation columns normally used for separation of fluids and can be either the packed or tray type or they can be a combined packed-tray type. Distillation column 20 will contain from about 10 to about 20 plates and preferably about 15 plates. Distillation column 27 requires only about 15 plates. Distillation column 27 requires only about 5 plates for satisfactory operation. However, from 5 to 10 plates can be employed if desired. The associated condensers employed with either or both of the distillation columns described are of generally conventional design and manufacture. Various pumps, compressors, reboilers etc. normally employed in carrying out distillations in chemical processes are employed in the process described herein. Since these do not form part of the invention, the details of their use in various phases of the process description have not been included.

The temperatures and pressures employed in the distillation zones of the present invention as described above will vary considerably depending on the particular carboxylic acid being produced. As a practical matter, the distillation zones are most often operated at pressures from about atmospheric to about 100 psig. The pressure employed in column 20 for example, when acetic acid is the carboxylic acid produced is from about 5 to about 20 psig and in column 27 it is about 30 – 35 psig with this acid. However, sub-atmospheric pressures may be employed if desired as well as superatmospheric pressures well in excess of 100 psig in either or both of these columns.

Temperatures within the distillation zones will normally lie between approximately atmospheric temperature and at or slightly above the boiling point of the particular carboxylic acid being recovered and purified. When employing the process in the manufacture of acetic acid, the bottoms temperature of column 20, for example, will generally be within the range from 120° to 135° C but preferably will be maintained at about 130° C. The bottoms temperature of column 27 will generally be higher and will be in the range from about 130° to about 140° C and preferably is maintained at about 136° – 139° C. The temperatures at the top of the distillation zones can likewise vary. Overhead temperatures in column 20, for example, in the process wherein acetic acid is produced can be from about 100° to about 120° and preferably are maintained at about 112° C to 116° C. In column 27, over head temperatures are lower being in the range of 75° C to 85° C and preferably about 80° C.

The point of introduction of the feed stream to the first distillation zone (column 20) can be anywhere intermediate the ends of the zone but the feed stream preferably is introduced into the lower half of that zone. The feed stream to the second distillation zone (column 27) can be introduced anywhere in the upper half of that zone. Generally, this feed is introduced at a point about two-thirds of the height of that distillation zone or into the upper one-third thereof.

The slipstream 26 removed from the heavy phase overhead of the first distillation zone may vary in the size from about 0.1 to about 1.0% by weight of the total heavy phase. For most efficient removal of alkanes, however, this stream constitutes from about 0.3 to about 0.5% by weight of the heavy phase.

The carbon monoxide introduced into the distillation zone to facilitate the removal of alkanes is generally fed at a rate to provide from about 0.01 to about 1 lb. of CO per pound of feed introduced into the zone. Other gases can be used for stripping if desired such as hydrogen and $CO_2$, for example.

To demonstrate the effectiveness and to illustrate the application of the process improvement of the present invention, the following non-limiting example is set forth. Unless otherwise indicated, all parts and percentages given are on a weight basis.

EXAMPLE 1

Methanol was carbonylated in the presence of a catalyst system that formed on mixing rhodium iodide with methyl iodide in the presence of carbon monoxide in an acetic acid-water reaction medium using apparatus substantially the same as is presented in the drawing. Approximately 267 parts/hr. of methanol were charged to the reactor 10 through line 12 while 244 parts/hr. of carbon monoxide were charged to the reactor through line 11. The reactor was maintained at a temperature of about 187° C and a pressure of about 400 psig. Unreacted carbon monoxide was withdrawn from the reactor through line 13 and passed to a flare. Approximately 5545 parts/hr. of liquid reaction mass was withdrawn from the reactor through line 14 and passed into separation zone 16. The pressure in separation zone 16 was about 20 psig and the liquid temperature was about 127° C. No heat was added to transfer line 14 or separation zone 16. The overhead vapor product containing 8% of acetic acid, 15% H$_2$O, 34% methyl iodide, 2% alkanes, and 0.02% hydrogen iodide, leaving separation zone 16 via line 17 is introduced at a rate of about 1748 parts/hr. into distillation column 20 having about 15 plates at about the second plate. About 3843 parts/hr. of unvaporized liquid reaction mass containing the stable homogeneous catalyst system was recirculated through line 18 to the reactor 10.

In distillation column 20 operated at about 17 psig, an overhead temperature of about 118° C and a bottoms temperature of about 129° C, acetic acid, water and some hydrogen iodide were separated from the other products in the reaction effluent and removed as the bottoms stream for return to the separation zone 16 via line 22 at a rate of about 28 parts/hr. The overhead from column 20 containing 52% methyl iodide, 3% alkanes, 22% acetic acid and 23% water was condensed and introduced into a separator 23 where it formed two phases. The light phase consisting essentially of 44% acetic acid and 49% water and 7% methyl iodide was returned to the reactor 10 by way of line 24.

The major part of the heavy phase containing approximately 87% methyl iodide, 3.64% alkanes, 3.5% acetic acid, 5% methyl acetate and 0.9% H$_2$O was returned to the reactor 10. A slipstream 26 of this heavy phase constituting about 0.4% of the total heavy phase was withdrawn through line 26 and introduced in column 27, a five-plate column at about the fourth plate at a rate of about 2.4 parts/hr. A stream of carbon monoxide was sparged into column 27 at the lower end via line 28 at a rate of 0.075 parts/hr. The overhead temperature in column 27 was maintained at about 75° C while the bottoms stream was kept at 142° C. The mid column temperature was 90° C. The overhead product consisting of 94% methyl iodide, 5% methyl acetate, and 1% water was withdrawn at a rate of about 2.3 parts/hr. and recycled to the separation zone. The bottoms product containing 43% alkanes, 52% acetic acid and traces of methyl iodide was continously removed from the system through line 30 at a rate of 0.1 part/hr. and burned.

It will be seen from the above data that the alkanes present in the reactor effluent are continuously removed by the process of the invention thus preventing their build-up in the system and obviating the problems arising therefrom.

What is claimed is:

1. In a carbonylation process for the production of carboxylic acids wherein a compound selected from the group consisting of compounds having the formulas: ROH wherein R is a saturated hydrocarbyl radical of 1 to 20 carbon atoms, R'—O—R' wherein R' is a saturated hydrocarbyl radical of 1 to 19 carbon atoms and wherein the total number of carbon atoms in the compound does not exceed 20, $$R'-\overset{\overset{O}{\|}}{C}-O-R'$$

wherein R' is a saturated hydrocarbyl radical of 1 to 19 carbon atoms and wherein the total number of carbon atoms in the compound does not exceed 20, and R—X wherein R is a saturated hydrocarbyl radical of 1 to 20 carbon atoms and X is a halogen selected from the group consisting of chlorine, bromine and iodine, is reacted with carbon monoxide or with carbon monoxide and water when said compound has the formula R'—O—R', $$R'-\overset{\overset{O}{\|}}{C}-O-R'$$

or R—X in the liquid phase in a reaction zone in the presence of a catalytic system which contains a rhodium or iridium component and an iodine or bromine component, and wherein a portion of the liquid reaction mass is passed to a separation zone without the addition of heat, said separation zone having a pressure of at least 20 psi less than the pressure in said reaction zone, to vaporize at least a portion of the carbonylation products, the remaining liquid reaction mass is recycled to the reaction zone and the vaporized carbonylation products are withdrawn and subjected to distillation for purification thereof, the improvement which comprises removing alkanes from the vaporized carbonylation products by introducing said vaporized carbonylation products into the lower half of a first distillation zone and distilling therein under conditions to provide an overhead product containing substantially all the alkanes introduced into said zone, and a bottoms product, removing said overhead product, condensing it, and separating it into a light phase and a heavy phase containing substantially all of said alkanes, withdrawing a slipstream constituting from about 0.1 to about 1% by weight of said heavy phase, introducing said slipstream into the upper section of a second distillation zone while introducing a stripping gas into the lower part of said second distillation zone and distilling therein to provide an overhead stream substantially free of alkanes and a bottoms stream consisting substantially of alkanes, recycling said alkane-free overhead stream from said second distillation zone to said separation zone, and removing said alkane-containing stream for disposal.

2. The process of claim 1 wherein said stripping gas introduced into the lower part of said second distillation zone is carbon monoxide.

3. The process of claim 2 wherein said bottoms product from said first distillation zone is recycled to said separation zone.

4. The process of claim 3 wherein said light phase from said overhead product of said first distillation zone is recycled to said reaction zone.

5. The process of claim 4 wherein the remainder of said heavy phase is recycled to said reaction zone.

6. The process of claim 5 wherein methanol is reacted with carbon monoxide in the presence of a catalyst system containing rhodium iodide and methyl iodide to produce acetic acid.

7. The process of claim 5 wherein methanol is reacted with carbon monoxide in the presence of a catalyst system containing iridium chloride and hydrogen iodide to produce acetic acid.

* * * * *